United States Patent
Wei et al.

(10) Patent No.: US 9,427,543 B2
(45) Date of Patent: Aug. 30, 2016

(54) INTUBATION DEVICE AND METHOD

(71) Applicants: Deye Wei, Brooklyn, NY (US); Chapman Wei, Brooklyn, NY (US); Chaplin Wei, Brooklyn, NY (US)

(72) Inventors: Deye Wei, Brooklyn, NY (US); Chapman Wei, Brooklyn, NY (US); Chaplin Wei, Brooklyn, NY (US)

(*) Notice: Subject to any disclaimer, the term of this patent is extended or adjusted under 35 U.S.C. 154(b) by 249 days.

(21) Appl. No.: 14/269,473

(22) Filed: May 5, 2014

(65) Prior Publication Data
US 2014/0238390 A1     Aug. 28, 2014

(51) Int. Cl.
*A61M 16/04*     (2006.01)
*A61B 1/267*     (2006.01)

(52) U.S. Cl.
CPC .......... *A61M 16/0488* (2013.01); *A61B 1/267* (2013.01); *A61B 1/2673* (2013.01)

(58) Field of Classification Search
CPC .. A61B 1/00032; A61B 1/0607; A61B 1/07; A61B 1/267; A61B 1/2673; A61B 1/2676; A61M 16/0418; A61M 16/0434; A61M 16/0488; A61M 2205/0266; A61M 25/00; A61M 25/01; A61M 25/01; A61M 16/0463
USPC ............ 128/200.26, 204.18, 207.14, 207.16; 600/104, 114, 120, 121, 131, 139, 141, 600/156, 164, 182, 187, 188, 194, 197; 604/164.01, 164.12, 164.13, 166.01, 604/170.02, 93.01; 606/194
See application file for complete search history.

(56) References Cited

U.S. PATENT DOCUMENTS

| | | | |
|---|---|---|---|
| 4,699,138 A * | 10/1987 | Behrstock | A61M 16/0463 128/207.16 |
| 4,727,872 A * | 3/1988 | Hawk | A61M 16/0488 128/207.14 |
| 5,095,888 A | 3/1992 | Hawley | |
| 5,184,603 A * | 2/1993 | Stone | A61B 1/2676 600/193 |
| 5,431,152 A | 7/1995 | Flam et al. | |
| 5,665,052 A * | 9/1997 | Bullard | A61B 1/2676 600/114 |
| 5,921,917 A | 7/1999 | Barthel et al. | |
| 6,543,447 B2 * | 4/2003 | Pacey | A61B 1/05 128/200.26 |
| 6,655,377 B2 * | 12/2003 | Pacey | A61B 1/2676 128/200.26 |
| 7,563,227 B2 * | 7/2009 | Gardner | A61B 1/012 600/153 |
| 2009/0050146 A1 | 2/2009 | Smith | |
| 2013/0228179 A1 * | 9/2013 | Fischer, Jr. | A61M 16/0488 128/204.18 |

FOREIGN PATENT DOCUMENTS

EP     0030014 A1 *  6/1981  ............... A61B 1/07
WO    WO 9726036 A1 *  7/1997  ........ A61M 16/0488

* cited by examiner

*Primary Examiner* — Annette Dixon
(74) *Attorney, Agent, or Firm* — Walter J. Tencza, Jr.

(57) ABSTRACT

Intubation devices and method of intubation are provided for a medical provider to firmly hold an intubation stylet with the middle, the ring, and the little finger of one hand, point the tips of the intubation stylet and an endotracheal tube towards the opening of the trachea, and then advance the endotracheal tube over the stylet into the trachea with the index finger and the thumb of the same hand without an assistant to hold the stylet, while the user can use another hand to hold a laryngoscope to perform laryngoscopy to visualize the vocal cords during endotracheal intubation. The intubation device comprises a handle, a stylet holder, and an arm which is connected to both the stylet holder and the handle. The intubation device further includes a tube support, and a tube holder to further support the endotracheal tube.

27 Claims, 5 Drawing Sheets

INTUBATION DEVICE AND METHOD

FIELD OF THE INVENTION

This invention relates to improved devices and methods concerning endotracheal intubation for ventilation of a patient.

BACKGROUND OF THE INVENTION

Endotracheal intubation is a known procedure in which a medical provider inserts an endotracheal tube into the trachea of a patient to ventilate the patient with oxygen for life support or with inhalation anesthetic agents for general anesthesia. Endotracheal intubation is also called intubation in medical practice.

In current practice and technique, the medical provider uses his or her left hand to hold a laryngoscope to perform laryngoscopy to visualize the vocal cords which is the opening of the trachea, and uses his or her right hand to hold and insert both the endotracheal tube and a stylet together into the trachea through the vocal cords.

The stylet, which is also called the intubation stylet in medical practice, is generally malleable metal rod or wire, and used to insert into a lumen of an endotracheal tube to stiffen and reshape the endotracheal tube more curved in the front part of the endotracheal tube, or in a shape like a hockey stick, to facilitate the endotracheal tube to turn around the epiglottis and the tongue, and advance over the stylet into the trachea through the vocal cords.

As soon as the front part of the endotracheal tube passes through the vocal cords, the medical provider removes the laryngoscope, uses the left hand to hold the stylet, and then uses the right hand to advance the endotracheal tube over the stylet into the trachea. Sometimes, an assistant is needed to hold the stylet when the medical provider's left hand is still needed to hold the laryngoscope to visualize the vocal cords to make sure that the endotracheal tube is still advanced through the vocal cords, especially in a patient with a difficult airway.

In a situation of a difficult airway, the vocal cords are not visualized with a regular direct laryngoscope, because the vocal cords are located more anteriorly in the anatomy of the patient or the patient has a big tongue or a small chin in the anatomy of the patient. In another situation of a difficult airway, only a small part of the vocal cords is visualized. It may be difficult, or impossible, to insert the endotracheal tube through the vocal cords into the trachea of the patient, or it may be likely to cause mechanical damage to the vocal cords and the trachea during intubation. With use of a video laryngoscope, such as the GlideScope (Trademarked) video laryngoscope, even though the vocal cords are seen in a video screen, it may still be difficult, or even impossible, to insert the endotracheal tube through the vocal cords into the trachea, because of the anterior location of the vocal cords in the patient's anatomy and the difficulty for the endotracheal tube to be turned more around the epiglottis of the patient.

Some medical providers may place and point the tips of both the stylet and the endotracheal tube in direction towards the vocal cords under the epiglottis, and ask for an assistant to hold the stylet still, and then advance the endotracheal tube over the stylet into the trachea through vocal cords. Unfortunately, it may be difficult, or impossible, for the assistant to hold the stylet still and keep pointing the stylet in direction towards the vocal cords, because the assistant is unable to see the vocal cords at the same time and at the same angle as the intubation performer who is performing the laryngoscopy and the intubation. It is very difficult to have good communication and coordination between the intubation performer and the assistant to complete an intubation.

SUMMARY OF THE INVENTION

An intubation device of one or more embodiments of the present invention allows an user to hold a stylet with a intubation device, point the tips of both the stylet and the endotracheal tube towards the vocal cords with the middle finger, the ring finger and the little finger of the one hand, and at the same time, allows the user to use the user's index finger and the thumb of the same hand to advance the intubation tube over the stylet into the trachea through the vocal cords, without an assistant to hold the stylet.

At least one embodiment of the intubation device of the present invention provides a device, which is called an intubation device, to allow a user to hold a stylet with the intubation device, point the tips of both the stylet and the endotracheal tube towards the vocal cords with the middle finger, the ring finger and the little finger of the one hand of the user holding a handle of the intubation device, and at the same time, to allow the user to use his or her index finger and the thumb of the same hand to push the intubation tube over the stylet towards the vocal cords and advance the endotracheal tube into the trachea through the vocal cords, without an assistant to hold the stylet. In another words, the intubation device allows the user to use only one hand to hold the stylet still and point the tip of the stylet directly towards the vocal cords, and then advance the endotracheal tube over the stylet into the trachea without an assistant to hold the stylet.

Since the endotracheal tube is advanced over the stylet, while the stylet is held still, the endotracheal tube can be advanced and turned more around the epiglottis at a sharper angle during advancement of the endotracheal tube, so that the endotracheal tube is easier and more likely to be advanced into the trachea through the vocal cords, and less likely to cause mechanical trauma to the vocal cords, the trachea, and other parts of the airway, especially in a difficult airway intubation when a small part of the vocal cords or none of the vocal cords is visualized in laryngoscopy.

One embodiment of the intubation device comprises a handle, an arm, and a stylet holder. The handle has a top part. The arm has a front, and a rear. The front of the arm is affixed to the top part of the handle, while the rear of the arm is affixed to the stylet holder to allow the stylet holder to be located away from and posterior to the handle. The function of the arm is to position the stylet holder away from and posterior to the top part of the handle at a certain distance, such as about one to forty centimeters away from and posterior to the top part of the handle.

The intubation device further comprises a tube support, and a tube holder to further support the endotracheal tube and further increase stability of holding the endotracheal tube. The tube support has a front, and a rear. The rear of the tube support is affixed to the top part of the handle or to the front of the arm; the front of the tube support is affixed to the tube holder.

DETAILED DESCRIPTION OF THE DRAWINGS

Figure 1:
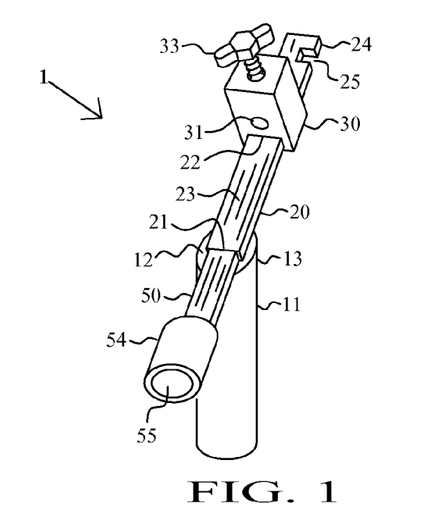
FIG. 1 is a front, top, and left side perspective view of a first intubation device in accordance with an embodiment of the present invention.
Figure 2:
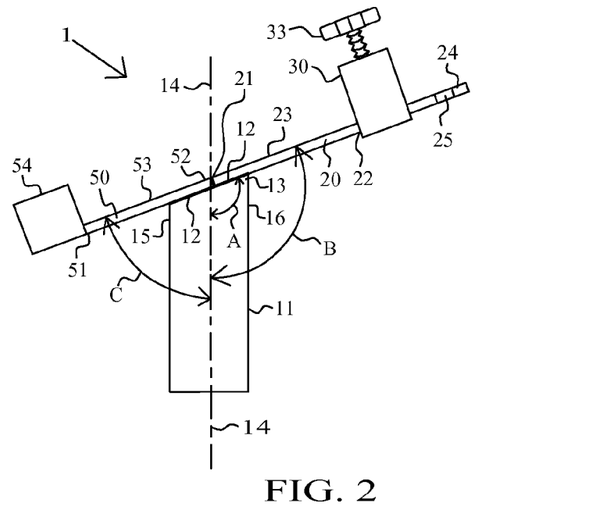
FIG. 2 is a left side view of the intubation device of FIG. 1.
Figure 3:
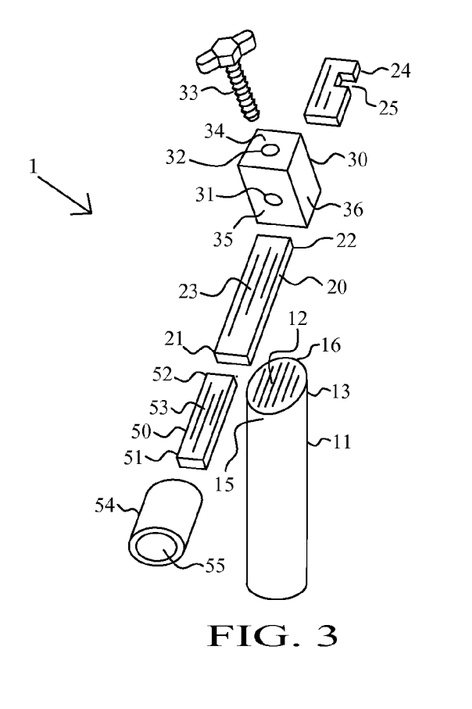
FIG. 3 is an exploded, front, top, and left side perspective view of the intubation device of FIG. 1.

FIG. 1 is a front, top, and left side perspective view of a first intubation device 1 of an embodiment of the present invention. FIG. 2 is a left side view of the first intubation device 1 of FIG. 1. FIG. 3 is an exploded, front, top, and left side perspective view of the first intubation device 1 of FIG. 1.

As shown in FIGS. 1, 2, and 3, the first intubation device 1 comprises a handle 11, an arm 20, a stylet holder 30, a tube support 50, and a tube holder 54. The stylet holder 30 further comprises a screw 33, or a stylet lock 24.

As shown in FIGS. 1, 2, and 3, one end of the arm 20 is affixed to the handle 11, while another end of the arm 20 is affixed to the stylet holder 30 to allow the stylet holder 30 to be located away from and posterior to the handle 11. One end of the tube support 50 is affixed to the handle 11, and/or to the arm 20, while another end of the tube support 50 is affixed to the tube holder 54. The stylet lock 24 is affixed to the stylet holder 30.

Figure 5:
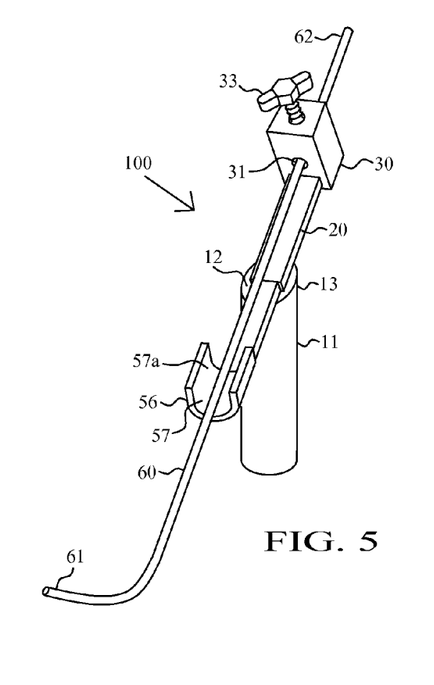
FIG. 5 is a front, top, and left side perspective view of the second intubation device of FIG. 4, along with a stylet inserted inside a stylet tunnel of a stylet holder.
Figure 6:
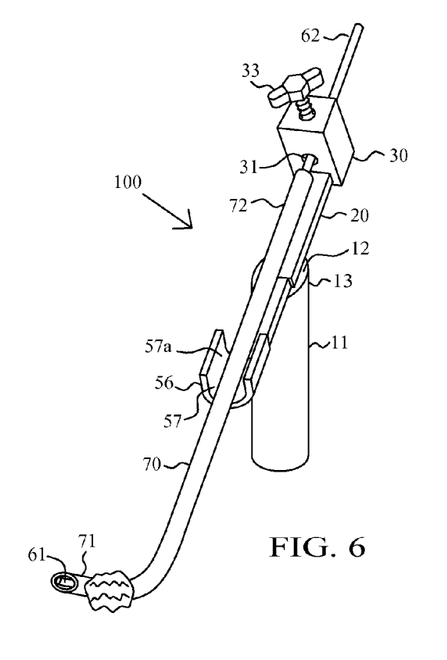
FIG. 6 is a front, top, and left side perspective view of the second intubation device of FIG. 4, the stylet shown in FIG. 5, and an endotracheal tube placed over the stylet.

The tube support 50, as well as the tube holder 54, further supports an endotracheal tube 70, shown in FIG. 6, when the user uses a stylet 60, shown in FIGS. 5 and 6, which is made of aluminum or plastic. The tube support 50, as well as the tube holder 54, is not included as a part of some other embodiments, especially, in at least one embodiment, when the user uses a stylet 60 which is made of steel. A steel stylet 60 is strong enough to support the endotracheal tube 70, shown in FIG. 6, without the tube support 50 and the tube holder 54, shown in FIG. 1.

In other embodiments, the handle 11, the arm 20, and the stylet holder 30 may be provided for an intubation device without the tube support 50 and the tube holder 54, and without other components shown in FIG. 1. In other embodiments, the handle 11, the arm 20, the stylet holder 30, and the tube support 50 may be provided for an intubation device without other components shown in FIG. 1.

Figure 4:
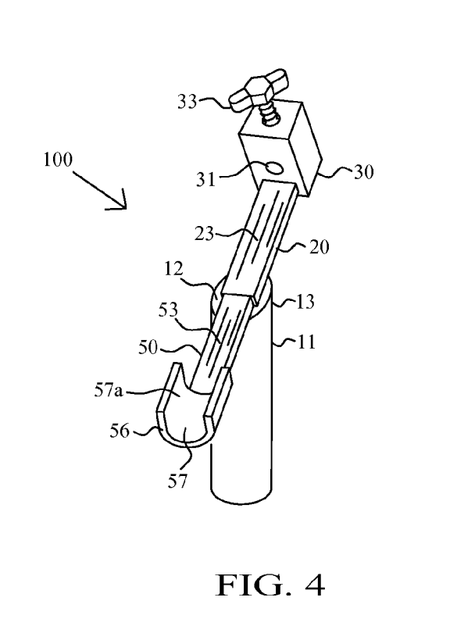
FIG. 4 is a front, top, and left side perspective view of a second intubation device in accordance with another embodiment of the present invention.

FIG. 4 is a front, top, and left side perspective view of a second intubation device 100, which comprises the handle 11, the arm 20, the stylet holder 30, the tube support 50, and a tube holder 56. In FIG. 4, the tube holder 56 is fixed to the tube support 50. In FIG. 4, the tube holder 56 is a modified structure of the tube holder 54 of FIG. 1, by cutting and opening the top of the tube holder 54, as will be described later in this application.

As shown in FIGS. 1, and 4, the difference between the first intubation device 1 of FIG. 1 and the second intubation device 100 of FIG. 4 is the difference between the tube holder 54 and the tube holder 56. As shown by the combination of FIGS. 1, and 4, when the tube holder 54 is cut and opened at the top of the tube holder 54 to have an opening at the top of the tube holder 54, the tube holder 54 becomes the tube holder 56. In another words, the tube holder 56 has an opening 57a at the top of the tube holder 56 as shown in FIGS. 4, 5, and 6.

Figure 7:
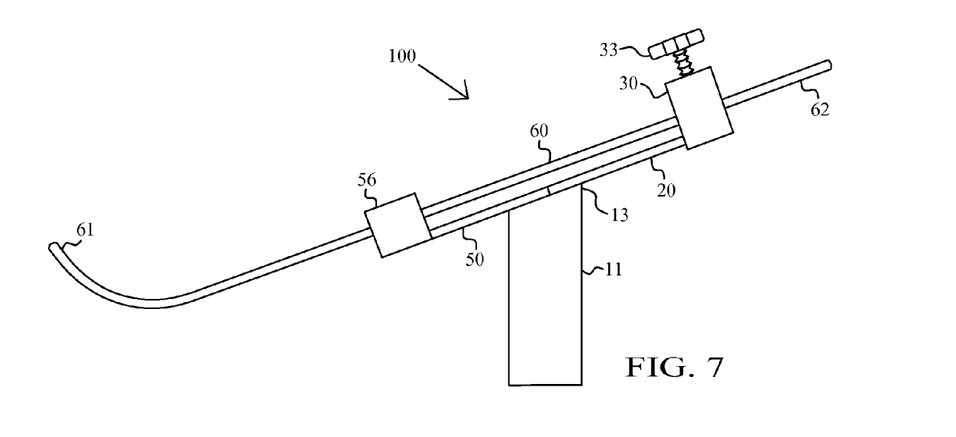
FIG. 7 is a left side view of the second intubation device of FIG. 4 and the stylet of FIG. 5.

FIG. 5 is a front, top, and left side perspective view of the second intubation device 100 of FIG. 4, with a stylet 60 held by the stylet holder 30. FIG. 7 is a left side view of the second intubation device 100 of FIG. 4, with the stylet 60 held by the stylet holder 30.

FIG. 6 is a front, top, and left side perspective view of the second intubation device 100 of FIG. 4, with the stylet 60 held by the stylet holder 30, and an endotracheal tube 70 placed over the stylet 60, wherein the stylet 60 is inserted into a lumen or inside space of the endotracheal tube 70.

Figure 8:
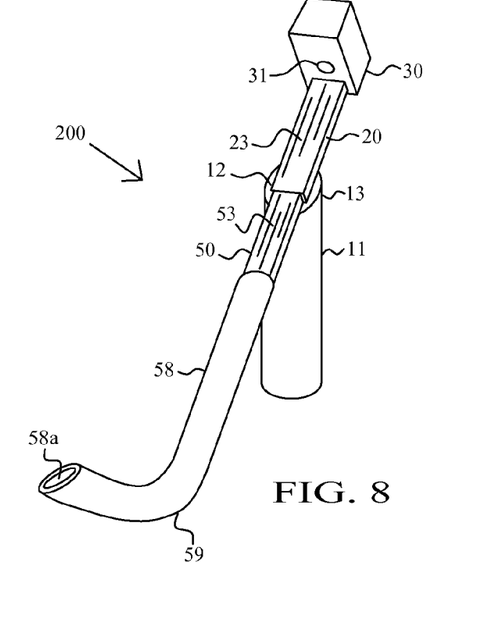
FIG. 8 is a front, top, and left side perspective view of a third intubation device in accordance with another embodiment of the present invention.

FIG. 8 is a front, top, and left side perspective view of third intubation device 200, in accordance with another embodiment of the present invention. As showed in FIG. 8, the embodiment of the third intubation device 200 of FIG. 8 comprises the handle 11, the arm 20, the stylet holder 30, the tube support 50, and a tube holder 58. The stylet holder 30 of the intubation device 200 of FIG. 8 does not have the screw 33. The tube holder 58 is affixed to the tube support 50. As shown in FIGS. 1 and 8, the difference between the embodiments of the first intubation device 1 of FIG. 1 and the third intubation device 200 of FIG. 8 is the difference between the tube holder 54 and the tube holder 58. The tube holder 58 is modified structure of the tube holder 54 by lengthening and bending the tube holder 54 like a hockey stick. The tube holder 58 is lengthened and bent like a hockey stick, compared to the tube holder 54.

The structures, connections, relations, and functions of each part of the intubation devices 1, 100, and 200 of embodiments of the present invention are described as follows:

(a) The Endotracheal Tube 70

Figure 17:
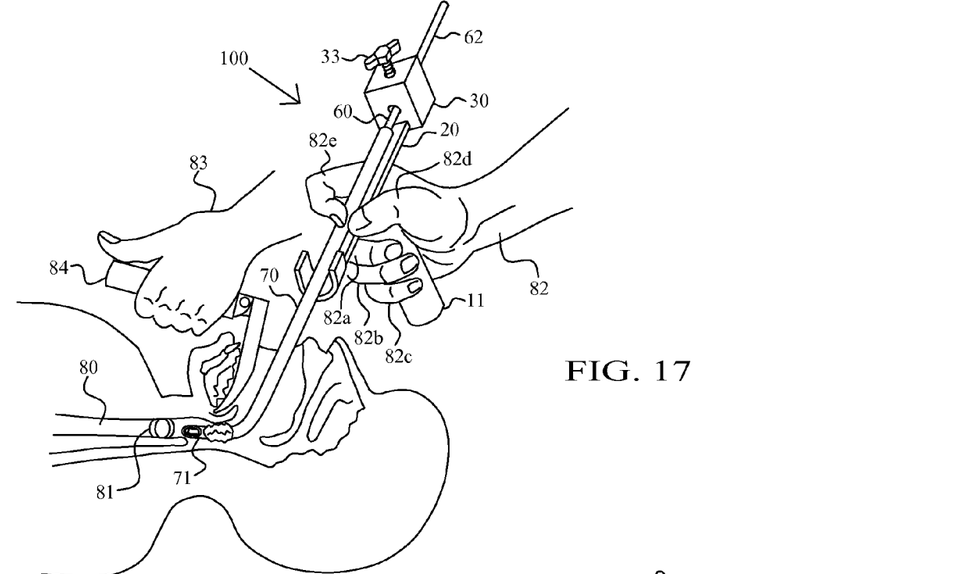
FIG. 17 is a left side view of an airway anatomy, and a front, top, and left side perspective view of the second intubation device of FIG. 6, with an user's right hand holding the second intubation device of FIG. 6, and pointing both tips of an endotracheal tube and a stylet in a direction towards the vocal cords during laryngoscopy and intubation.
Figure 18:
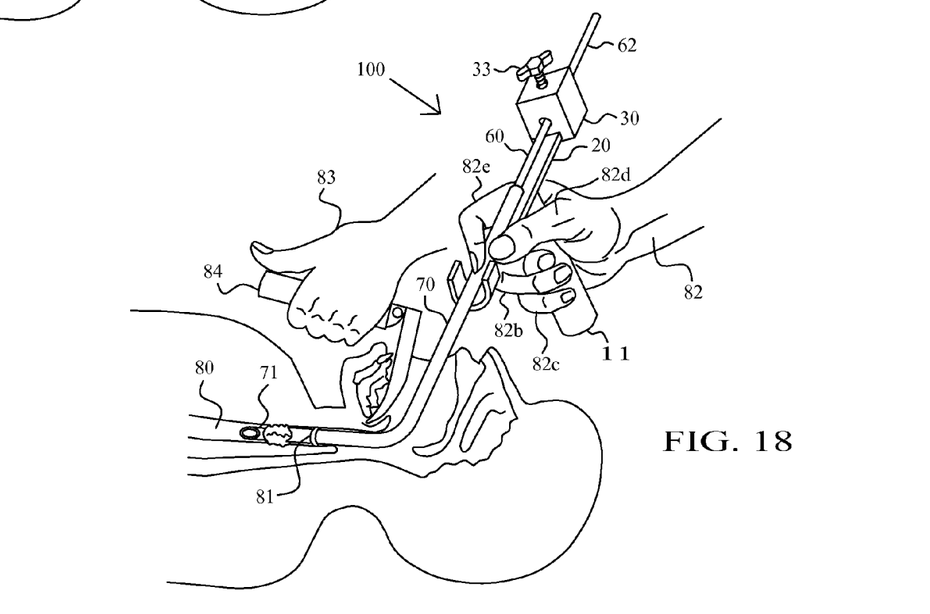
FIG. 18 is a left side view of an airway anatomy, and a front, top, and left side perspective view of the second intubation device of FIG. 6, with the middle finger, the ring finger, and the little finger of a user holding a handle of the second intubation device of FIG. 6, and the index finger and the thumb of the same hand advancing the endotracheal tube into the trachea.

The endotracheal tube 70 has a front part 71, a rear part 72, and a lumen, or opening or inner chamber, which is not labeled by number, as shown in FIGS. 6, 17, and 18. The endotracheal tube 70 is a soft plastic tube which is used for endotracheal intubation and usually inserted into the trachea of a patient for ventilation of the patient. The front part 71 of the endotracheal tube 70 is a part of the endotracheal tube 70 that is placed in the trachea of the patient, while the rear part 72 of the endotracheal tube 70 is a part of the endotracheal tube 70 that is placed outside the patient and is connected to a ventilator which ventilates the patient.

Many different types of endotracheal tubes, which are similar to or the same as the endotracheal tube 70, are known and have been used for endotracheal intubation in medical practice for many years. One of the endotracheal tubes commonly used in the United States of America now is the endotracheal tube made and sold by Covidien 11c, Mansfield, Mass. 02048.

(b) The Stylet 60

The stylet 60 has a front part 61, and a rear part 62 as shown in FIGS. 5 and 7. As shown in FIGS. 5, 6, 17, and 18, the stylet 60 is used to be inserted into the lumen or opening of the endotracheal tube 70 to stiffen the endotracheal tube 70, and bend the front part 71 of the endotracheal tube 70 as a hockey stick to facilitate the endotracheal tube 70 to turn around the epiglottis and the tongue and advance into the trachea through the vocal cords during endotracheal intubation. The front part 61 of the stylet 60 is a part of the stylet 60 that is placed inside the front part 71 of the endotracheal tube 70, while the rear part 62 of the stylet 60 is a part of the stylet 60 that is placed outside the rear part 72 of the endotracheal tube 70. Many different types of stylets, which are similar to or the same as the stylet 60, are known and have been used in medical practice for many years.

One type of stylet for use as the stylet 60, is a wire or a rod, and made of aluminum or other malleable metals allowing the stylet to be easily bent, and then to bend the front part 71 of the endotracheal tube 70 like a hockey stick, such as an intubation stylet made by Smiths Medical, 600 Cordwainer Drive, Norwell, Mass. 02061, U.S.A.

Another type of stylet for use as the stylet 60 is a wire or a rod, and made of steel, which has already been bent and shaped like a hockey stick around its front part, such as a stainless steel stylet which is made by Verathon, Inc, 20001 North Creek Parkway, Bothell, Wash. 98011, and commonly used with the GlideScope (Trademarked), a video laryngoscope, which is made by Verathon, Inc, 20001 North Creek Parkway, Bothell, Wash. 98011.

Another type of stylet for use as the stylet 60 is a wire or a rod, and made of plastic. The plastic stylet is a soft stylet, such as the Bougie Stylet and Eschmann stylet made by Smiths Medical, 5200 Upper Metro Place, Suite 200, Dublin, Ohio 43017. The plastic stylet is not strong enough to stiffen, bend or reshape the endotracheal tube 70. The plastic stylet is usually used to be inserted into the trachea first, and then used as a guide-wire for the endotracheal tube 70 to be inserted into the trachea over the plastic stylet.

Another type of stylet for use as the stylet 60, is a video equipped stylet, which has a camera at its tip to view the vocal cords, and show the vocal cords in a screen during intubation, such as a video stylet made by Karl Storz, Mittelstr. 8, 78532, Tuttlingen, Germany.

The stylet 60 can be the same as or similar to one of these types of stylets. All types of these stylets can be used with the intubation devices 1, 100, or 200 of embodiments of the present invention as the stylet 60 for intubation.

(c) The Handle 11

The handle 11 is a cylinder shaped structure for the user to hold the intubation device 1, 100, or 200, as shown in FIGS. 1, 2, 3, 4, 8, 17 and 18. However, the handle 11 can be ergonomically shaped differently to fit the user's hand to hold the handle 11.

As shown in FIGS. 1, 2 and 3, the handle 11 comprises a top surface 12 (shown in FIG. 3), a top part 13 which also includes the top surface 12, a long axis 14 (shown in FIG. 2), a front part 15, and a rear part 16. The front part 15 is a part of the handle 11 that is closest to the patient during intubation, while the rear part 16 is a part of handle 11 that is an opposite part of the front part 15 and is farthest away from the patient during intubation. As shown in FIGS. 2 and 3, the top surface 12 is so sloped that an angle A between the top surface 12 of the handle 11 and the long axis 14 of the handle 11 is approximately between one hundred degrees to one hundred and thirty degrees, as shown in the lateral view of FIG. 2, so that both the arm 20 and the tube support 50 can be affixed to the top surface 12 of the handle 11 to have the same sloped angle to allow the user to advance the endotracheal tube 70 with the thumb and the index finger more easily and comfortably. However, in another embodiment of the present invention, the angle A between the top surface 12 and the long axis 14 of the handle 11 can be about ninety degrees for the intubation device 1, 100, or 200 to function normally and satisfactorily.

As shown in FIGS. 17 and 18, the handle 11 allows a user to hold the second intubation device 100 with the middle finger 82a, the ring finger 82b, and the little finger 82c of one hand 82, so that the user is able to use the thumb 82d and the index finger 82e of the same hand 82 to advance the endotracheal tube 70 forward during intubation. The handle 11 even allows the user to hold the second intubation device 100 with only the ring finger 82b, and the little finger 82c of one hand 82, so that the user is able to use the middle finger 82a of the same hand 82 as the tube support 50 to further support the endotracheal tube 70, and use the thumb 82d and the index finger 82e of the same hand 82 to advance the endotracheal tube 70 forward during intubation.

(d) The Arm 20

The arm 20 is a cuboid structure which connects the stylet holder 30 to the handle 11 together, as shown in FIGS. 1, 2, and 3. However, in other embodiments, the structure of the arm 20 can be different, such as cylindrical, etc. The function of the arm 20 is to position the stylet holder 30 away from the rear part 16 of the handle 11 and posterior to the rear part 16 of the handle 11 at a certain distance.

The arm 20 comprises a front end 21, a rear end 22, and a top surface 23. The arm 20 is about one to forty centimeters long from the front end 21 to the rear end 22, so that the arm 20 allows the stylet holder 30 to be positioned about one to forty centimeters away from and posterior to the rear part 16 of the handle 11 to allow the stylet holder 30 to hold the rear part 62 of the stylet 60, shown in FIG. 5, about one to forty centimeters away from the handle 11 and posterior to the rear part 16 of the handle 11.

As shown in FIGS. 1, 2, 3 and 4, the front end 21 of the arm 20 is affixed to the top surface 12 of the handle 11, while the rear end 22 of the arm 20 is affixed to the stylet holder 30. However, in another embodiment of the present invention, the front end 21 of the arm 20 is affixed to the top part 13 of the rear part 16 of the handle 11 to function normally.

As shown in FIGS. 1, 2, 3, and 4, the front end 21 of the arm 20 is so affixed to the top surface 12 of the handle 11, or the top part 13 of the rear part 16 of the handle 11, that an angle B (shown in FIG. 2) between the top surface 23 of the arm 20 and the long axis 14 of the handle 11 is formed which is approximately between one hundred degrees to one hundred and thirty degrees, as shown in the lateral view of FIG. 2, so that the user uses their index finger and their thumb to advance the endotracheal tube 70 more easily and comfortably. However, the angle B between the top surface 23 of the arm 20 and the long axis 14 of the handle 11 can be about ninety degrees for the intubation device 1, 100, or 200 to function normally.

The shape of the cross section of the arm 20 is rectangular, as shown in FIG. 3. However, in other embodiments, the shape of the cross section of the arm 20 is different, such as circular, semicircular, and/or irregular.

(e) The Stylet Holder 30

Figure 9:
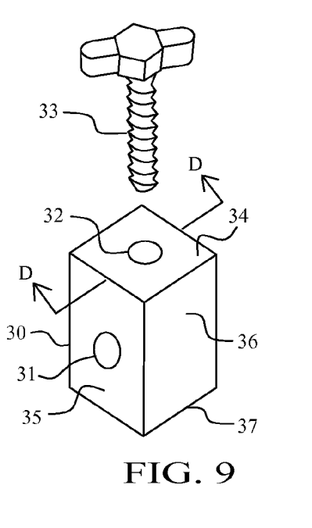
FIG. 9 is a front, top, and left side perspective view of a first stylet holder, along with a screw, for use with the first intubation device of FIG. 1 and the second intubation device of FIG. 4.
Figure 10:
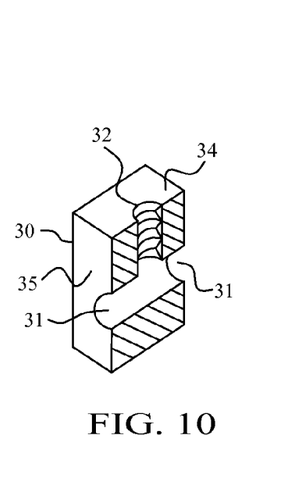
FIG. 10 is a partial, front, top, and left side perspective view and a cross-section view of the stylet holder of FIG. 9 along a line D-D as shown in FIG. 9, with the screw of FIG. 9 not being shown.

FIG. 9 is a front, top, and left side perspective view of a first stylet holder 30. FIG. 10 is a partial, front, top, and left side perspective view and a cross-section view of the first stylet holder of FIG. 9 along a line D-D as shown in FIG. 9. The stylet holder 30 is shown as a cuboid structure, in FIGS. 1, 2, 3, 4, 9, and 10. However, in other embodiments, the structure shape of the stylet holder 30 can be different, such as cylindrical, etc. The function of the stylet holder 30 is to hold the stylet 60 about one to ten millimeters above the arm 20 to allow the stylet 60 to be able to insert into the lumen or opening of the endotracheal tube 70, and to hold the rear part 62 of the stylet 60 about one to forty centimeters away from the handle 11, as shown in FIGS. 5, 6, and 7.

As shown in FIGS. 1, 2, 3, and 4, the stylet holder 30 is affixed to the rear end 22 of the arm 20. However, in other embodiments, the stylet holder 30 can be affixed to the top surface 23 of the arm 20.

FIG. 9 is a front, top, and left side perspective view of an embodiment of the stylet holder 30. FIG. 10 is a partial, front, top, and left side perspective view and a cross-section view of the stylet holder 30 of FIG. 9 along a line D-D as shown in FIG. 9.

As shown in FIGS. 3, 9, and 10, the stylet holder 30 comprises a top 34, a front 35, a left side 36, a bottom 37, a rear which is not shown, and a right side which is not shown. The stylet holder 30 further comprises a stylet tunnel 31. The stylet tunnel 31 opens from the front 35 of the stylet holder 30 and extends to the rear of the stylet holder 30. The long axis of the stylet tunnel 31 is about parallel to the long axis of the arm 20. The stylet tunnel 31 allows the rear part 62 of the stylet 60 be inserted into the stylet tunnel 31, so that the stylet holder 30 can hold the stylet 60 inside the stylet tunnel 31 as shown in FIGS. 5, 6, and 7.

The cross section shape of the stylet tunnel 31 is circular, as shown in FIGS. 3, 9, and 10. However, in other embodiments, the cross section shape of the stylet tunnel 31 can be different, such as triangular, rectangular, etc. The stylet tunnel 31 offers a space for the rear part 62 of the stylet 60 to be placed in and held by the stylet holder 30. The shape of the cross section of the stylet tunnel 31 can be the same as or different from the shape of the cross section of the rear part 62 of the stylet 60.

The size, or the diameter, of the stylet tunnel 31 is bigger than the size, or the diameter, of the rear part 62 of the stylet 60 so that the rear part 62 of the stylet 60 can be placed into and removed from the stylet tunnel 31 easily. However, the size, or the diameter, of the stylet tunnel 31 may be the same, in at least one embodiment, as the size, or the diameter, of the rear part 62 of the stylet 60 so that the stylet 60 can be placed into and held in the stylet tunnel 31 tight.

The stylet holder 30 may further comprise a screw nut hole 32, and a screw 33, as shown in FIGS. 1, 2, 3, 4, and 9. The screw nut hole 32 is a screw nut for the screw 33 to function. The screw 33 can be turned and driven through the screw nut hole 32 and into the stylet tunnel 31 to compress and tighten the stylet 60 inside the stylet tunnel 31, so that the stylet 60 is not able to move back and forth, as shown in FIGS. 5, 6, and 7. The screw nut hole 32 is positioned at the top 34 of the stylet holder 30 as shown at FIGS. 3, 9, and 10. However, in another embodiment, the screw nut hole 32 can be positioned at the left side 36, or the right side, or the bottom 37 of the stylet holder 30.

Figure 11:
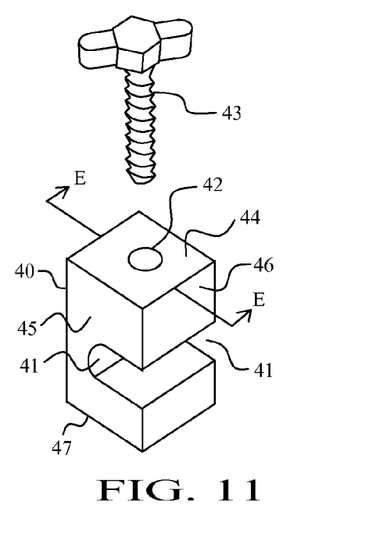
FIG. 11 is a front, top, and left side perspective view of a second stylet holder for use in place of the first stylet holder, wherein the second stylet holder has an opened stylet tunnel.
Figure 12:
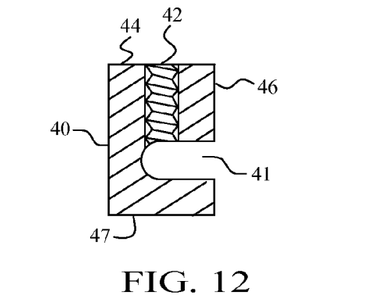
FIG. 12 is a partial, front, top, and left side perspective view and a cross-section view of the second stylet holder of FIG. 11 along a line E-E as shown in FIG. 11, with the screw of FIG. 11 not being shown in FIG. 12.

FIG. 11 is a front, top, and left side perspective view of a second stylet holder 40 for use in place of the first stylet holder 30. FIG. 12 is a partial, front, top, and left side perspective view and a cross-section view of the second stylet holder 40 along a line E-E as shown in FIG. 11.

As showed in FIGS. 11 and 12, the stylet holder 40 comprises a stylet tunnel 41, a screw nut hole 42, a screw 43, a top 44, a front 45, a left side 46, a bottom 47, a rear which is not shown, and a right side which is not shown. As showed in FIGS. 11 and 12, the stylet tunnel 41 has an opening at its left side 46 and has a structure like a groove, or a gap. The opening of the stylet tunnel 41 allows the stylet 60 to be placed into the stylet tunnel 41 more easily than the embodiment of the first stylet holder 30 of FIG. 9. In another embodiment, the stylet tunnel 41 may have the opening at the top 44, or the right side of the stylet holder 40.

The stylet holder 30 can be modified to become the stylet holder 40. When stylet tunnel 31 is cut and opened at one side, such as the left side 36, to form an opening to have a structure like a groove, or a gap, then the stylet tunnel 31 becomes the stylet tunnel 41, and the stylet holder 30 becomes the stylet holder 40, as shown in the combination of FIGS. 9, 10, 11 and 12.

In case that the stylet tunnel 31, or the stylet tunnel 41 is too small for the rear part 62 of the stylet 60 to be placed in, the user can use a tape, such as a surgical tape, to affix the rear part 62 of the stylet 60 onto the top 34 of the stylet holder 30, or the top 44 of the stylet holder 40. If an embodiment of the stylet holder 30 does not have a stylet tunnel like the stylet tunnel 31 to hold the rear part 62 of the stylet 60, the user can use a tape, such as a surgical tape, to affix the rear part 62 of the stylet 60 onto the top 34 of the stylet holder 30.

In another embodiment of the intubation device, the stylet 60 is affixed to the stylet holder 30 together when the intubation device, such as the intubation device 1, and 100, is made.

(f) The Stylet Lock 24

Figure 13:
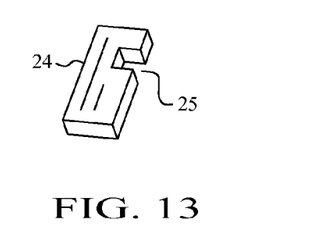
FIG. 13 is a front, top, and left side perspective view of a stylet lock.
Figure 14:
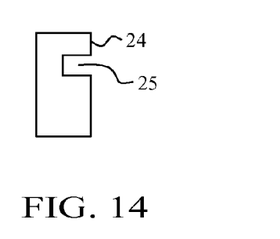
FIG. 14 is a top view of the stylet lock of FIG. 13.

As shown in FIGS. 3, 13, and 14, the stylet lock 24 is a cuboid structure comprising a stylet gap 25. The gap 25 is a cut, or an opening, to allow the rear part 62 of the stylet 60 to be bended and placed in. The size of the gap 25 is bigger than the diameter of the rear part 62 of the stylet 60 to allow the rear part 62 of the stylet 60 to be able to be placed in. As shown by one or more of FIGS. 1, 2, 3, and 15, the stylet lock 24 is affixed to the rear of the stylet holder 30 below the stylet tunnel 31. However, in another embodiment, the stylet lock 24 may be affixed to the rear of the stylet holder 30 above the stylet tunnel 31.

Figure 15:
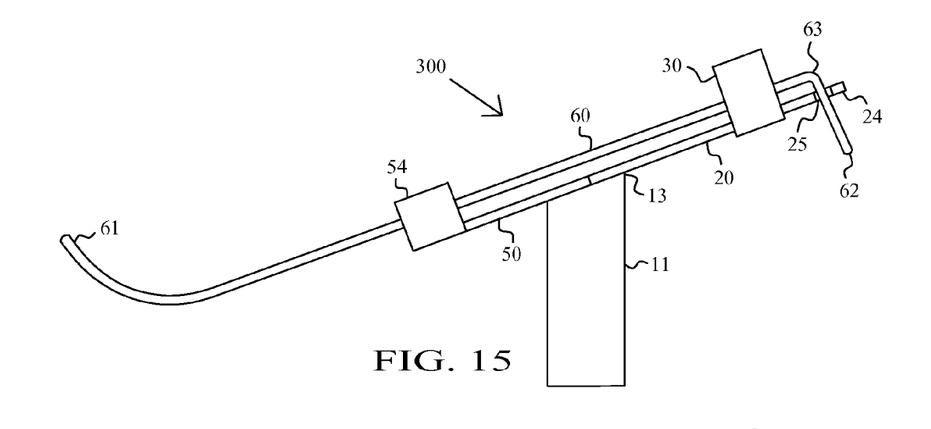
FIG. 15 is a left side view of a fourth intubation device, in accordance with another embodiment of the present invention, with a stylet inserted inside a stylet tunnel of a stylet holder which does not have a screw, and with a rear part of the stylet placed in a stylet lock.

The function of the stylet lock 24 is to allow the bended rear part 62 of the stylet 60 to be placed in the stylet gap 25 to stop the stylet 60 from moving back and forth during intubation, as shown in FIGS. 1, and 15. The stylet lock 24 adds on one more mechanism to the stylet holder 30 for the stylet holder 30 to stop the stylet 60 from moving back and forth as the screw 33 shown in FIGS. 1, 4, and 5 does.

FIG. 15 is a left side view of a fourth intubation device 300, with the stylet 60 inserted inside the stylet tunnel 31 of the stylet holder 30, and the bended rear part 62 of the stylet 60 placed in the stylet gap 25 of the stylet lock 24, wherein the stylet holder 30 does not include the screw 33 as a part.

As shown in FIG. 15, the stylet 60 is placed into the stylet tunnel 31 of the stylet holder 30, and then bended at a part 63 of the stylet 60, and the bended rear part 62 of the stylet 60 is placed in the stylet gap 25 of the stylet lock 24, so that the stylet 60 is not able to move back and forth, without the screw 33. In one or more embodiments of the present application, if an intubation device has the stylet lock 24, it is not necessary for it to have the screw 33 to hold the stylet 60 securely in the stylet holder 30.

Since the stylet lock 24 and the screw 33 have the same function, in one or more embodiments, which is to stop the stylet 60 from moving back and forth inside the stylet tunnel 31 of the stylet holder 30, the stylet holder 30 can include both or one of the screw 33 and the stylet lock 24.

Figure 16:
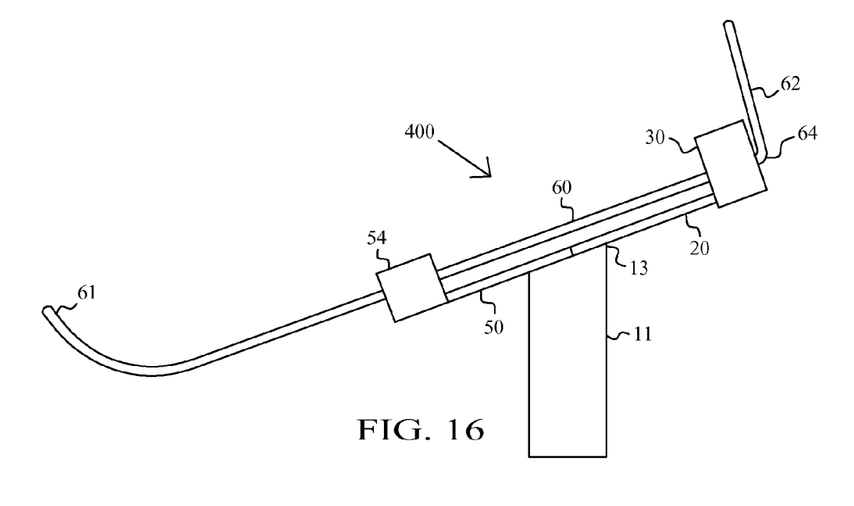
FIG. 16 is a left side view of a fifth intubation device in accordance with another embodiment of the present invention, with a stylet inserted inside a stylet tunnel of a stylet holder which does not have a screw and a stylet lock.

FIG. 16 is a left side view of a fifth intubation device 400, with the stylet 60 inserted inside the stylet tunnel 31 of the stylet holder 30, wherein the stylet holder 30 does not include either the screw 33 or the stylet locker 24. The rear part 62 is bended up at a part 64 of the stylet 60 for the rear part 62 of the stylet 60 to be secured in the stylet holder 30 without either the screw 33 or the stylet lock 24, so that the stylet 60 is not able to move forward when the endotracheal tube 70 is advanced forward into the trachea 80 during intubation, as referred in FIGS. 16, 17, and 18.

(g). The Tube Support 50

As shown in FIGS. 1, 2, 3, 4, 5, and 6, the tube support 50 is a cuboid structure similar to, or about the same as the structure of the arm 20. The tube support 50 comprises a front 51, a rear 52, and a top surface 53. The tube support 50 is about one to fifteen centimeters long. The rear 52 of the tube support 50 is affixed to the top surface 12 of the handle 11 or is affixed to the front end 21 of the arm 20. The long axis of the tube support 50 is approximately parallel to the long axis of the arm 20. The top surface 53 of the tube support 50 is approximately at the same level of the top surface 23 of the arm 20 to allow the endotracheal tube 70 to be advanced on smoothly.

The function of the tube support 50 is to further support the endotracheal tube 70 when the user uses a stylet 60 which is made of aluminum or plastic, and is easily bended, as shown in FIGS. 6, 17, and 18. The tube support 50 is not included as a part of some embodiments if these embodiments are made for use with a stylet 60 which is made of steel, since a steel stylet 60 is strong enough to support the endotracheal tube 70 securely without the tube support 50. The user can also use the user's middle finger 82a in place of the tube support 50 to further support the endotracheal tube 70 as the tube support 50 does during intubation, as shown by FIGS. 17 and 18.

As shown in FIGS. 1, 2, and 3, the tube support 50 is so affixed to the top surface 12 of the handle 11, or the front end 21 of the arm 20, that an angle C (shown in FIG. 2) between the top surface 53 of the tube support 50 and the long axis 14 of the handle 11 is approximately between fifty degrees to eighty degrees as shown by the lateral view as shown in FIG. 2, and that the top surface 53 of the tube support 50 is approximately at the same level of the top surface 23 of the arm 20, to allow the index finger and the thumb of the user to advance the endotracheal tube 70 more easily and comfortably. The cross section shape of the tube support 50 is rectangular, as shown in FIG. 3. However, in another embodiment, the cross section shape of the tube support 50 can be different, such as circular, semicircular, etc.

(h.) The Tube Holder 54, the Tube Holder 56, and the Tube Holder 58

The tube holder 54 is a structure of a pipe, or a tube, which has a lumen, or a tunnel, as shown in FIGS. 1, 2, and 3. The tube holder 54 is affixed to the front 51 of the tube support 50. The lumen, or the tunnel, is called a tube tunnel 55 which has a bigger diameter than the diameter of the endotracheal tube 70 to allow the endotracheal tube 70 to be inserted into the tube tunnel 55 of the tube holder 54 easily. The function of the tube holder 54 is to prevent and/or inhibit the endotracheal tube 70 from moving substantially from side to side when the user uses a stylet 60 which is made of aluminum or plastic, and is easily bended, as shown in FIGS. 6, 17, and 18.

The tube holder 56 is used in another embodiment to hold the endotracheal tube 70 instead of the tube holder 54. As shown in FIGS. 4, 5, and 6, the tube holder 56 comprises a tube tunnel 57 or slot 57, which is a hollow part of the tube holder 56 to allow the endotracheal tube 70 to be placed in. The tube tunnel 57 or slot 57 has the opening 57a. The opening 57a of the tube tunnel 57 is larger than the diameter of the endotracheal tube 70 to allow the endotracheal tube 70 to be placed into and removed from the tube tunnel 57 of the tube holder 56 easily.

The tube holder 54 can be modified to become a tube holder 56, as shown by the combination of FIGS. 1 and 4. As shown by FIGS. 1 and 4, when the tube holder 54 is cut and opened at the top of the tube holder 54 to allow the tube tunnel 55 to have an opening, the tube holder 54 becomes the tube holder 56.

The tube holder 58 is another embodiment to hold the endotracheal tube 70 instead of the tube holder 54, as shown in FIG. 8. The tube holder 58 is a structure of a pipe, or a tube, with a lumen 58a which has a bigger diameter than the diameter of the endotracheal tube 70 to allow the endotracheal tube 70 to be inserted into the lumen 58a of the tube holder 58 easily. The tube holder 58 has a bended part 59 where the tube holder 58 is bended like a hockey stick, as shown in FIG. 8. The tube holder 54 can be modified by lengthening and bending like a hockey stick in shape to become the tube holder 58.

As shown in FIG. 8, the tube holder 58 is lengthened, bended, and shaped like a hockey stick to further bend the front part 71 of the endotracheal tube 70 like a hockey stick to facilitate the endotracheal tube 70 to turn around the epiglottis and advance into the trachea without the stylet 60 or with a soft plastic stylet, such as the Bougie stylet (Trademarked). As shown in FIGS. 1, and 8, the difference between the embodiments of the intubation device 1 of FIG. 1 and the intubation device 200 of FIG. 8 is the difference between the tube holder 54 and the tube holder 58 in length and shape.

As shown in FIG. 8, the rear 52 of the tube support 50 is affixed to the front 21 of the arm 20 and/or the top surface 12 of the handle 11, while the front end 51 of the tube support 50 is affixed to the tube holder 58. However, in another embodiment, which is not shown in drawings, the rear end 52 of the tube support 50, which is lengthened, is affixed to the front 34 or the top 35 of the stylet holder 30, while the front end 51 of the tube support 50 is affixed to the tube holder 58.

To use the intubation devices 1, 100, 200, 300, and/or 400 of one or more embodiments of the present invention for intubation, a user, usually a medical provider, such as an anesthesiologist, or a physician of an emergency room, needs to assemble the stylet 60, the endotracheal tube 70, and one of the intubation devices 1, 100, 200, 300, and 400 together as one unit, as the first step.

To assemble the stylet 60, the endotracheal tube 70, together with one of the intubation devices 1, 100, 200, 300, and 400, for example the embodiment of the intubation device 100 of FIG. 4, as one unit, the user inserts the rear part 62 of the stylet 60 into the stylet tunnel 31 of the stylet holder 30, as shown in FIGS. 5 and 7, and then inserts the stylet 60 into the lumen of the endotracheal tube 70, as shown in FIG. 6.

The user turns and drives the screw 33 down through the screw nut hole 32 to compress and tighten the rear part 62 of the stylet 60 inside the stylet tunnel 31 of the stylet holder 30 to stop the stylet 60 from moving inside the stylet tunnel 31 of the stylet holder 30, as shown in FIG. 6, for using the embodiment in which the stylet holder 30 has the screw 33.

For using the embodiment which has the stylet holder 40 as shown in FIGS. 11 and 12, the rear part 62 of the stylet 60 is placed into the stylet tunnel 41 of the stylet holder 40 through the opening of the stylet tunnel 41. The screw 43 is turned and driven down to compress and tighten the rear part 62 of the stylet 60 inside the stylet tunnel 41 of the stylet holder 40.

For using the embodiment which has the tube holder 54, as shown in FIGS. 1, 2, and 3, the endotracheal tube 70 is inserted through the tube tunnel 55 of the tube holder 54 at the same time as the stylet 60 is inserted into the lumen of the endotracheal tube 70.

For using the embodiment which has the tube holder 56 in which the tube tunnel 57 has the opening 57a, as shown in FIG. 4, the endotracheal tube 70 is placed into the tube tunnel 57 of the tube holder 56 through the opening 57a of the tube tunnel 57 as shown in FIGS. 4, 5, and 6.

To use the embodiment which has the stylet lock 24, which is shown in FIGS. 1, 2, 3, 13, and 14, the rear part 62 of the stylet 60 is bended down at the part 63 of the stylet 60, and placed in the stylet gap 25 of the stylet lock 24 to stop the stylet 60 from moving back and forth during intubation, as shown in FIG. 15.

To use the embodiment which does not have the screw 33 and the stylet lock 24, the rear part 62 of the stylet 60 is bended up at the part 64 of the stylet 60 to stop the stylet 60 moving forward during intubation, as shown in FIG. 16.

When the stylet tunnel 31, or the stylet tunnel 41 is too small for the stylet 60 to be placed in, the user can use a tape, such as a surgical tape, to tape and affix the stylet 60 onto the top 34 of the stylet holder 30, or the top 44 of the stylet holder 40.

If the user uses the stylet 60 which is made of aluminum or other malleable metals, the user bends both the front part 61 of the stylet 60 and the front part 71 of the endotracheal tube 70 together like a hockey stick in shape, as shown in FIG. 6, after the stylet 60 is inserted into the lumen of the endotracheal tube 70.

When the user uses an embodiment which does not have the tube support 50, the tube holder 54 or the tube holder 56, the user can use his or her middle finger 82a to further support the endotracheal tube 70 as the tube support 50 does during intubation, as referred in FIGS. 17 and 18.

After the first step that the user has assembled the stylet 60, the endotracheal tube 70, and one of the intubation devices 1, 100, 200, 300, or 400 together as one unit, as shown in FIG. 6, for an example, the user can start the second step to use the intubation device to perform intubation as follows.

As the second step, the user grasps the handle 11 with the middle finger 82a, the ring finger 82b and the little finger 82c of the right hand 82, and holds the endotracheal tube 70 with the thumb 82d and the index finger 82e of the same right hand 82, as showed in FIGS. 17 and 18. The user can test movement the endotracheal tube 70 over the stylet 60 by pushing and withdrawing the endotracheal tube 70 over the stylet 60 back and forth with the thumb 82d and index finger 82e.

During intubation as shown in FIG. 17, the user holds a laryngoscope 84 with the left hand 83 to perform laryngoscopy to visualize the vocal cords 81, which is the opening of the trachea 80 and usually located under the epiglottis in human's anatomy. After the user visualizes the vocal cords 81, the user points both the front part 71 of the endotracheal tube 70 and the front part 61 of the stylet 60 in direction towards the vocal cords 81, and then pushes the endotracheal tube 70 with the index finger 82e and the thumb 82d, and advances the endotracheal tube 70 over the stylet 60 into the trachea 80 through the vocal cords 81, as shown in FIG. 18, while the stylet 60 is held and maintained still by the user holding the handle 11 still.

When the user can not visualize the vocal cords 81 in a difficult airway, but the user can visualize the epiglottis, during laryngoscopy, the user places both the front part 71 of the endotracheal tube 70 and the front part 61 of the stylet 60 under the epiglottis, and then advances the endotracheal tube 70 over the stylet 60 into the trachea 80 in direction to the vocal cords 81 with the index finger 82e and the thumb 82d as an attempt at blind intubation, since the vocal cords 81 is usually located under the epiglottis in human's anatomy, as shown in FIGS. 17 and 18. If the user feels significant resistance when he or she advances the endotracheal tube 70, he or she withdraws the endotracheal tube 70 back over the stylet 60 with the index finger 82e and the thumb 82d, changes the position and direction of both the front part 71 of the endotracheal tube 70 and the front part 61 of the stylet 60 by manipulating the handle 11, and then advances the endotracheal tube 70 over the stylet 60 forwards again as another attempt at blind intubation, as shown in FIGS. 17 and 18, until the endotracheal tube 70 is advanced into the trachea 80 successfully.

To use the intubation device 200 of FIG. 8, which has the lengthened and bended tube holder 58 like a hockey stick, as shown in FIG. 8, the user inserts the front part 61 of the plastic stylet 60, such as the Bougie (trademarked) Stylet, into the lumen of the endotracheal tube 70, and then inserts both the plastic stylet 60 and the endotracheal tube 70 together into the lumen 58a of the tube holder 58, and the rear part 62 of the plastic stylet 60 into the stylet tunnel 31 of the stylet holder 30. The user can also insert only the endotracheal tube 70 into the lumen 58a of the tube holder 58 without using the plastic stylet 60, since the tube holder 58 is already bended and shaped like the hockey stick to further bend the endotracheal tube 70. The user grasps the handle 11 with the middle finger 82a, the ring finger 82b and the little finger 82c of the right hand 82, and holds the endotracheal tube 70 with the thumb 82d and the index finger 82e of the same right hand 82.

After the user visualizes the vocal cords 81 during laryngoscopy, the user points the front part 71 of the endotracheal tube 70 to the vocal cords 81, and then pushes the endotracheal tube 70 with the index finger 82e and the thumb 82d into the trachea 80 through the vocal cords 81, while the tube holder 58 is held and maintained still by the user holding the handle 11 still. If the vocal cords 81 are partially visualized in a difficult airway, the plastic stylet 60 can be advanced into the trachea 80 first by an assistant, and then the endotracheal tube 70 is advanced over the plastic stylet 60 into the trachea 80 with the index finger 82e and the thumb 82d, since the plastic stylet 60 is smaller than the endotracheal tube 70 and easier to be advanced into the trachea 80 through the vocal cords 81 than the endotracheal tube 70.

Another way to use the intubation device 200 of FIG. 8 is described as follows. The user inserts only the plastic stylet 60 into the lumen 58a of the tube holder 58 and the stylet tunnel 31 of the stylet holder 30. The user grasps the handle 11 with the middle finger 82a, the ring finger 82b and the little finger 82c of the right hand 82, and holds the plastic stylet 60 with the thumb 82d and the index finger 82e of the same right hand 82. After the user visualizes the vocal cords 81, or small part of the vocal cords 81, during laryngoscopy, the user points the tip of the plastic stylet 60 in direction towards the vocal cords 81, and then pushes the plastic stylet 60 with the index finger 82e and the thumb 82d into the trachea 80 through the vocal cords 81. Then, the user removes the intubation device 200 of FIG. 8, and uses the plastic stylet 60 as a guide-wire to advance the endotracheal tube 70 over the plastic stylet 60 into the trachea 80.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

We claim:

1. An intubation device for use with a stylet having a rear part, and an endotracheal tube having a lumen for endotracheal intubation to ventilate a patient, the intubation device comprising:
   a handle having a top part, a front part, a rear part, and a long axis;
   an arm having a top surface, a front end, and a rear end, with the front end of the arm being affixed to the top part of the handle and the rear end of the arm being located posterior to the rear part of the handle;
   a tube support having a top surface, a front end, and a rear end, with the rear end of the tube support being affixed to the top part of the handle and the front end of the tube support being located in front of the front part of the handle;
   and a means for holding the stylet above the arm, wherein the means is affixed to the rear end of the arm;
   wherein the arm is substantially linear, and is fixed to the handle at an orientation with respect to the handle such that an angle between the top surface of the arm and the long axis of the handle is approximately ninety degrees;
   wherein the tube support is substantially linear; and is fixed to the handle at an orientation with respect to the handle such that an angle between the top surface of the tube support and the long axis of the handle is approximately ninety degrees, and the tube support is substantially aligned with the arm.

2. The intubation device of claim 1 wherein
the means for holding the stylet includes a stylet holder having a front, and a rear, and being securely affixed to the rear end of the arm; and whereby the stylet holder is configured to hold the stylet above the arm, and to hold the rear part of the stylet away from and posterior to the handle.

3. The intubation device of claim 2 wherein
the stylet holder comprises a stylet tunnel which opens from the front of the stylet holder and extends to the rear of the stylet holder;
wherein a long axis of the stylet tunnel is about parallel to a long axis of the arm;
and wherein the stylet tunnel allows the stylet to be inserted into the stylet tunnel so that the stylet holder can hold the stylet inside the stylet tunnel.

4. The intubation device of claim 3 wherein
the stylet tunnel is cut and opened to have an opening as a groove for the stylet to be placed in and removed from the stylet tunnel through the opening.

5. The intubation device of claim 2 wherein
the stylet holder further comprises a screw nut hole, and a screw which can be turned and driven through the screw nut hole into the stylet tunnel to compress the stylet inside the stylet tunnel to stop the stylet from moving back and forth.

6. The intubation device of claim 2 wherein
the stylet holder further comprises a stylet lock which has a stylet gap to allow the rear part of the stylet to be bended and placed in the stylet gap to stop the stylet from moving back and forth, wherein the stylet lock is affixed to the rear of the stylet holder.

7. The intubation device of claim 1 wherein
the handle includes a top surface;
wherein the top surface of the handle is so sloped that an angle between the top surface of the handle and the long axis of the handle is approximately ninety degrees, so that the arm is affixed to the top surface of the handle to have the same sloped angle.

8. The intubation device of claim 1 wherein
the arm is so affixed to the top part of the handle that an angle between the top surface of the arm and the long axis of the handle is approximately ninety degrees.

9. The intubation device of claim 1 wherein
the arm has a length;
the tube support has a length;
the handle has a height; and
a combination of the length of the arm together with the length of the tube support is greater than the height of the handle.

10. The intubation device of claim 1 wherein
the tube support is so affixed to the top part of the handle that a top surface of the tube support and the top surface of the arm are approximately at the same level to allow the endotracheal tube to be advanced smoothly.

11. The intubation device of claim 1 further comprising
a tube holder which has a tube tunnel to hold the endotracheal tube to prevent the endotracheal tube from moving from side to side, wherein the tube holder is affixed to the front end of the tube support.

12. The intubation device of claim 11 wherein
the tube holder is cut opened for the tube tunnel to have an opening for the endotracheal tube to be placed in and removed from the tube tunnel.

13. The intubation device of claim 11 wherein
the tube holder is bent in an L-shape to further bend the endotracheal tube in an L-shape.

14. The intubation device of claim 1 further comprising the stylet held in the means for holding the stylet.

15. An intubation device for use with a stylet having a rear part, and an endotracheal tube having a lumen for endotracheal intubation to ventilate a patient, the intubation device comprising:
- a handle having a top part, a front part, a rear part, and a long axis;
- a tube support having a top surface, a front end, and a rear end, with the rear end of the tube support being affixed to the top part of the handle and the front end of the tube support being located in front of the front part of the handle;
- a stylet holder having a front, and a rear;
- and an arm having a top surface, a front end, and a rear end, with the front end of the arm being affixed to the top part of the handle and the rear end of the arm being affixed to the stylet holder;
- wherein the stylet holder is configured to hold the stylet above the arm, and to hold the rear part of the stylet away from and posterior to the rear part of the handle,
- wherein the arm is substantially linear, and is fixed to the handle at an orientation with respect to the handle such that an angle between the top surface of the arm and the long axis of the handle is approximately ninety degrees; and
- wherein the tube support is substantially linear; and is fixed to the handle at an orientation with respect to the handle such that an angle between the top surface of the tube support and the long axis of the handle is approximately ninety degrees, and the tube support is substantially aligned with the arm.

16. The intubation device of claim 15 wherein
the stylet holder comprises a stylet tunnel which opens from the front of the stylet holder and extends to the rear of the stylet holder;
wherein a long axis of the stylet tunnel is about parallel to a long axis of the arm; and
wherein the stylet tunnel allows the stylet to be inserted into the stylet tunnel so that the stylet holder can hold the stylet inside the stylet tunnel.

17. The intubation device of claim 16 wherein
the stylet tunnel is cut and opened to have an opening as a groove for the stylet to be placed in and removed from the stylet tunnel through the opening.

18. The intubation device of claim 15 wherein
the stylet holder further comprises a screw nut hole, and a screw which can be turned and driven through the screw nut hole into the stylet tunnel to compress the stylet inside the stylet tunnel to stop the stylet from moving back and forth.

19. The intubation device of claim 15 wherein
the stylet holder further comprises a stylet lock which has a stylet gap to allow the rear part of the stylet to be bended and placed in the stylet gap to stop the stylet from moving back and forth, wherein the stylet lock is affixed to the rear of the stylet holder.

20. The intubation device of claim 15 wherein
the handle has a top surface;
and wherein the top surface of the handle is so sloped that an angle between the top surface of the handle and the long axis of the handle is approximately ninety degrees, so that the arm is affixed to the top surface of the handle to have the same sloped angle.

21. The intubation device of claim 15 wherein
the arm is so affixed to the top part of the handle that an angle between the top surface of the arm and the long axis of the handle is approximately ninety degrees.

22. The intubation device of claim 15 wherein
the arm has a length;
the tube support has a length;
the handle has a height; and
a combination of the length of the arm together with the length of the tube support is greater than the height of the handle.

23. The intubation device of claim 15 wherein
the tube support is so affixed to the top part of the handle that a top surface of the tube support and the top surface of the arm are approximately at the same level to allow the endotracheal tube to be advanced smoothly.

24. The intubation device of claim 15 further comprising a tube holder which has a tube tunnel to hold the endotracheal tube to prevent the endotracheal tube from moving from side to side, wherein the tube holder is affixed to the front of the tube support.

25. The intubation device of claim 24 wherein
the tube holder is cut opened for the tube tunnel to have an opening for the endotracheal tube to be placed in and removed from the tube tunnel.

26. The intubation device of claim 24 wherein
the tube holder is bent in an L-shape to further bend the endotracheal tube in an L-shape.

27. The intubation device of claim 15 further comprising the stylet held in the stylet holder.

* * * * *